（12） United States Patent
Sabin et al.

(10) Patent No.: US 10,220,197 B2
(45) Date of Patent: Mar. 5, 2019

(54) PERCUTANEOUS CONNECTION DEVICE WITH A SOCKET AND WITH AN EXTENSION MEMBER

(71) Applicant: UBIPLUG, Saint-Contest (FR)

(72) Inventors: Pierre Sabin, Rouen (FR); Pierre-Yves Quelenn, Petit Quevilly (FR)

(73) Assignee: PLUGMED HEART (FR)

( * ) Notice: Subject to any disclaimer, the term of this patent is extended or adjusted under 35 U.S.C. 154(b) by 535 days.

(21) Appl. No.: 14/410,872

(22) PCT Filed: Jun. 28, 2013

(86) PCT No.: PCT/EP2013/063623
§ 371 (c)(1),
(2) Date: Dec. 23, 2014

(87) PCT Pub. No.: WO2014/001501
PCT Pub. Date: Jan. 3, 2014

(65) Prior Publication Data
US 2015/0320991 A1    Nov. 12, 2015

Related U.S. Application Data

(60) Provisional application No. 61/676,975, filed on Jul. 29, 2012, provisional application No. 61/665,866, filed on Jun. 28, 2012.

(51) Int. Cl.
*A61M 39/02* (2006.01)
*A61N 1/05* (2006.01)

(52) U.S. Cl.
CPC ....... *A61M 39/0247* (2013.01); *A61N 1/0539* (2013.01); *A61M 2039/025* (2013.01);
(Continued)

(58) Field of Classification Search
CPC ........ A61M 39/0247; A61M 2039/025; A61M 2039/0261; A61M 2039/0267;
(Continued)

(56) References Cited

U.S. PATENT DOCUMENTS 4,004,298 A * 1/1977 Freed ................ A61M 39/0247
285/9.1
4,328,813 A   5/1982 Ray
(Continued)

OTHER PUBLICATIONS

International Search Report for Application No. PCT/EP2013/063623 dated Jan. 31, 2014.

*Primary Examiner* — Bradley J Osinski
*Assistant Examiner* — Nilay Shah
(74) *Attorney, Agent, or Firm* — Lerner, David, Littenberg, Krumholz & Mentlik, LLP

(57) ABSTRACT

A percutaneous connection device to be fixed in an osseous structure of a patient to connect an internal entity located inside the body of the patient to an entity external to said body, the device comprising a percutaneous socket having a first end comprising a percutaneous abutment and a second end opposite to the first end, an elongated extension member designed to be inserted within a hole created into the osseous structure, said extension member having a first end to be removably coupled to the second end of the socket and a second end opposite to the first end, an anchoring mechanism for anchoring the device to the osseous structure by osseointegration and a separate connection running through the device from the first end of the percutaneous socket to the second end of the extension member, and comprising at least a first connector arranged within the percutaneous abutment.

31 Claims, 12 Drawing Sheets

(52) U.S. Cl.
CPC ............... *A61M 2039/0261* (2013.01); *A61M 2039/0267* (2013.01); *A61M 2205/0238* (2013.01); *A61M 2205/04* (2013.01); *A61M 2207/00* (2013.01)

(58) Field of Classification Search
CPC ...... A61M 2039/0238; A61M 2205/04; A61M 2039/0276; A61M 2039/0279; A61N 1/0539; A61N 1/0558; A61B 17/8875
See application file for complete search history.

(56) References Cited

U.S. PATENT DOCUMENTS

| | | | | |
|---|---|---|---|---|
| 5,242,431 | A * | 9/1993 | Kristiansen | A61M 25/02 128/DIG. 26 |
| 5,352,204 | A * | 10/1994 | Ensminger | A61M 39/0208 604/175 |
| 5,782,645 | A * | 7/1998 | Stobie | A61N 1/02 439/289 |
| 5,817,984 | A * | 10/1998 | Taylor | H01B 17/305 174/152 GM |
| 5,904,646 | A * | 5/1999 | Jarvik | A61M 39/0247 600/16 |
| 5,993,448 | A | 11/1999 | Remmler | |
| 6,018,094 | A | 1/2000 | Fox | |
| 7,074,222 | B2 * | 7/2006 | Westerkull | A61F 2/141 606/312 |
| 2005/0075680 | A1 * | 4/2005 | Lowry | A61N 1/0531 607/45 |

\* cited by examiner

PERCUTANEOUS CONNECTION DEVICE WITH A SOCKET AND WITH AN EXTENSION MEMBER

CROSS REFERENCE TO RELATED APPLICATIONS

The present application is a national phase entry under 35 U.S.C. § 371 of International Application No. PCT/EP2013/063623 filed Jun. 28, 2013, published in English, which claims the benefit of the filing date of the U.S. Provisional Patent Application No. 61/665,866 filed Jun. 28, 2012, and U.S. Provisional Patent Application No. 61/676,975 filed Jul, 29, 2012, the disclosures of which are hereby incorporated herein by reference.

FIELD OF THE INVENTION

The present invention relates to the implantation of medical devices in the body of an animal, in particular in the human body, especially the implantation of connection devices, more particularly to set up a connection transfer energy and/or of matter between an external element and a medical apparatus implanted in the body.

TECHNICAL BACKGROUND

The substantial development made in electrical equipment designed to be installed inside the body of a patient to rectify failure of a natural organ already implies a capability for transmitting electric power required by this equipment, from a source of external power to the interior of the body.

Contactless power-supply techniques using power transmission via transformer already exist. Power-supply techniques via percutaneous cranial connectors are also known.

U.S. Pat. No. 5,904,646 discloses in particular a percutaneous socket enabling an electrical connection between an apparatus implanted in the body of a patient, and an external apparatus such as power supply. This percutaneous socket is fixed onto the surface of an osseous wall by means of an osteosynthesis screw, with all the elements making up the socket and the cables being therefore subcutaneous, that is, essentially in the zone of the dermis. However, such an arrangement of the socket is not sufficiently reliable and vulnerable to infections propagated from percutaneous passage.

Patent FR 03-04063 and patent application U.S. Ser. No. 12/631,161 disclose a permanent percutaneous connector and associated method to set up an epithelial seal, which is advantageous to prevent propagation of infections from the percutaneous passage. However, such arrangement requires a bone augmentation around the percutaneous passage which might increase the duration of the surgical procedure.

An aim of the present invention is to propose a permanent percutaneous electrical connection device that can address at least one of the above identified drawbacks.

In particular, an aim of the present invention is to propose a permanent percutaneous electrical connection device which is very reliable, that limit the risks of infection, and that might be positioned easily and quickly by a practitioner.

SUMMARY OF THE INVENTION

To this end, there is provided a percutaneous connection device as defined in the appended claims.

In particular, there is provided a percutaneous connection device, preferably intended to transfer energy or matter, intended to be fixed in an osseous structure of a patient to connect an internal entity located inside the body of the patient to an entity external to said body, wherein the device comprises:
- a percutaneous socket having a first end comprising a percutaneous abutment and a second end opposite to the first end;
- an elongated extension member designed to be inserted within a hole created into the osseous structure, said extension member having a first end comprising means to be removably coupled to the second end of the socket, and a second end opposite to the first end, the removable coupling of the extension member relative to the percutaneous socket being designed for angular shifting of the first end of the percutaneous socket relative to the second end of the extension member;
- anchoring means provided for anchoring the device to the osseous structure by osseointegration; and
- separate connection means running through the device from the first end of the percutaneous socket to the second end of the extension member, said connection means comprising at least a first connector arranged within the percutaneous abutment.

Preferable but not limited aspects of such device, taken alone or in combination, are the following:
- the angular shifting of the first end of the percutaneous socket relative to the second end of the extension member is at least of 70°, preferably lower than 110°, even more preferably comprised between 90° and 100°, and most preferably of 95°.
- the extension member is removably fastened to the percutaneous socket, and the anchoring means are arranged at the second end of the percutaneous socket, said second end of the percutaneous socket being designed for osseous burial in the osseous structure so that the percutaneous abutment protrudes relative to the surface of the osseous structure.
- the percutaneous socket is removably fastened to the extension member, and the anchoring means are arranged at the first end of the extension member, close to the removable coupling of the extension member relative to the percutaneous socket.
- the extension member and the percutaneous socket are removably coupled via an anchoring base comprising the anchoring means, said anchoring base being designed for osseous burial in the osseous structure and comprising first coupling means for removable fastening of the percutaneous abutment intended to protrude relative to the surface of the osseous structure, and second coupling means for removable fastening of the extension member intended to be fully buried in the osseous structure. Such device may preferably have the following features:
  - the anchoring base comprises an implant having a cylindrical or truncated-conical shape, said implant having at least one hole provided in a wall of the implant;
  - the percutaneous abutment has a shape to be at least partially inserted in the implant;
  - the first end of the elongated extension member comprises means to be removably inserted within the hole of the implant.
- the implant comprises a threaded portion for implantation into the osseous structure, and a ring portion at one end of the implant for tightening and adjusting the position of the implant into the osseous structure.
- the ring portion comprises at least one lateral flat portion.

the implant comprises a plurality of anchoring holes provided in a lateral wall of the implant, each of said anchoring holes being intended to receive an osteosynthesis screw for anchoring the implant into the osseous structure.

the abutment comprises a through hole for reception of the first connector, said through hole having a shape designed for guiding positioning of the first connector within the abutment.

the anchoring means comprises a plurality of osteosynthesis screws intended to protrude relative to the surface the device in order to mesh with a lateral wall of a cavity of the osseous structure.

the anchoring means comprises at least one anchoring element arranged so as to be able to protrude relative to the surface the device in order to mesh with a lateral wall of a cavity of the osseous structure.

the anchoring means comprises a threaded surface, said threaded surface easing primary anchoring of the device in the osseous structure.

the anchoring element comprises projecting portions, said projecting portions being designed to penetrate the lateral wall of the cavity in a depth between 20 micrometers and 2000 micrometers, and preferably in a depth of 400 micrometers.

the projecting portions have a geometric shape to provide a retention effect, said shape being preferably a symmetric shape chosen among a cone shape, a pyramid shape, and/or a polyhedron shape.

the percutaneous socket, the percutaneous abutment, the implant, and/or the extension member are made of titanium, polyether ether ketone, zirconia and/or any biocompatible material.

the implant is made of titanium using machining and/or additive manufacturing processes.

the implant and/or the extension member is coated with a coating for promoting osseointegration of the device into the osseous structure.

the percutaneous abutment can be connected mechanically, magnetically, and/or physically to one or multiple external parts.

the first connector is clipped within the percutaneous abutment with a non-return system.

the first connector is maintained in position within the percutaneous abutment with a maintaining element inserted within the percutaneous abutment.

the maintaining element is a ring screwed or pushed in the abutment, said ring preferably comprising a cutting on the inside in order to place an O-ring to maintain the first connector in compression.

the extension member has a tubular lumen geometry, said tubular lumen geometry being chosen among parallelepipedal, regular polygonal, irregular polygonal circular, ovaloid, round or a combination thereof.

the extension member comprises a plurality of tubes.

the tubes are arranged parallel to each other.

the first connector is connected to an intermediate connector by a ribbon cable made of biocompatible electrical wires, encapsulated with silicon or any other material that is both flexible and biocompatible.

the device comprises an intermediate connector intended to be connected to the internal entity, wherein said intermediate connector comprises a screw or pin system to lock and seal the intermediate connector.

the device comprises an intermediate connector intended to be connected to the internal entity, wherein said intermediate connector comprises at least one eyelet on each side, said eyelets being used to attach the implant to the bone with screw and/or suture the implant to the fascia.

the abutment is partly and/or totally cylindrical, triangular and/or polygonal.

the connection means comprises a second connector arranged at the opposite end of the connection means relative to the first connector, said second connector having a shape designed to pass through the percutaneous socket and the extension member.

the connection means are electrical connection means, and the first connector and/or the second connector are jack connectors, preferably having a cross-section being circular or in cross arrangement.

According to another aspect, there is provided a percutaneous connection device, preferably intended to transfer energy or matter, intended to be fixed in an osseous structure of a patient to connect an internal entity located inside the body of the patient to an entity external to said body, wherein the device comprises:

an implant having a cylindrical or truncated-conical shape, said implant forming an anchoring base with anchoring means for anchoring of the device in the osseous structure, and said implant having at least one lateral hole provided in a lateral wall of the implant;

a percutaneous abutment having a shape to be at least partially inserted in the implant, preferably in a removable manner;

an elongated extension member intended to be inserted within a hole created into the osseous structure, said extension member having a first end comprising means to be removably inserted within the lateral hole of the implant, and a second end opposite to the first end; and connection means running through the device from the percutaneous abutment to the second end of extension member, said connection means comprising at least a first connector arranged within the percutaneous abutment.

There is also provided a percutaneous endosseous connection assembly (100) intended to be fixed in an osseous structure of a patient to electrically connect an internal entity (150) located inside the body of the patient to an entity external to said body, characterized in that the device comprises an endosseous implant (131) in which is inserted a percutaneous abutment (111) adapted to be connected to the external entity, and an electrical connection element (130) adapted to be coupled to the internal entity (150), the abutment (111) coupled to an extension member (115), buried in the osseous structure, which extremity emerging under the skin is separated from the abutment by a non-zero distance, the whole implant, abutment (111), extension member (115) and emerging extremity ensuring the gateway of the electrical connections means between the percutaneous connector (100) and the intermediate connector (138, 140).

There is further provided a percutaneous endosseous connection device (100) intended to be fixed in an osseous structure of a patient to transfer liquids to an internal entity (150) to an entity external to said body and/or extract liquids from an internal entity (150) located inside the body of the patient to an entity external to said body. The said connection is characterized in that the device comprises a percutaneous connector (100) adapted to be connected to the external entity, and tube elements adapted to be coupled to the internal entity (150), the abutment (111) coupled to an extension member (115), buried in the osseous structure, which extremity emerging under the skin is separated from the abutment by a non-zero distance, that extremity of the extension member, the whole connector extension (115) and emerging extremity ensuring the gateway of the tube connections means between the percutaneous connector (100) and the intermediate connector or directly the internal entity (150).

There is also provided a percutaneous endosseous connection device (100) intended to be fixed in an osseous structure of a patient to transfer light (fiber optics and/or other means) to an internal entity (150) located inside the body of the patient to an entity external to said body, characterized in that the device comprises a percutaneous connector (100) adapted to be connected to the external entity, and tube elements adapted to be coupled to the internal entity (150), the abutment (111) coupled to an extension member (115), buried in the osseous structure (1), which extremity emerging under the skin is separated from the abutment by a non-zero distance, that extremity (125) of the extension member, the whole connector extension (115) and emerging extremity ensuring the gateway of the light connections means between the percutaneous connector (100) and the intermediate connector or directly the internal entity (150).

Preferable but not limited aspects of such percutaneous endosseous connection devices, taken alone or in combination, are the following: the implant is made of titanium using machining and/or additive manufacturing processes, the surface of the implant received a coating, the implant is made of polyether ether ketone, zirconia and/or any biocompatible material, the socket (110) can be connected mechanically, magnetically, and/or physically to one or multiple external parts, the implanted cable(s) (135, 145) can be maintained in the intermediate connector by a mechanical element (clipped, screwed, impacted), the abutment (111) and the tubular extension (115) form a single-piece element, the abutment (111) and the tubular extension (115) do not form a single-piece element, the abutment (111) and the implant (131) form a single-piece element, the abutment (111) and the implant (131) do not form a single-piece element, the abutment (111) and the electrical connection (130) form a single-piece element, the abutment (111) and the electrical connection (130) do not form a single-piece element, the tubular extension can be characterized by different lumen geometries, including in particular: parallelepipedal, regular polygonal, irregular polygonal circular, ovaloid, round and/or any combination thereof to form a multiple lumen tubular extension, the tubular extension can consist of several tubes, a connector (130), that can be subcutaneous, is connected to the percutaneous connector (100) by a ribbon cable made of biocompatible electrical wires, encapsulated with silicon or any other material that is both flexible and biocompatible. The connector would comprise a screw or pin system to lock and seal the subconnector. The connector would comprise one eyelet on each side. The said eyelets being used to attach the implant to the bone with screw and/or suture the implant to the fascia. The abutment (111) is partly and/or totally cylindrical, triangular and/or polygonal.

BRIEF DESCRIPTION OF THE DRAWINGS

Other characteristics and advantages of the invention will become clear from the following description which is only given for illustrative purposes and is in no way limitative and should be read with reference to the attached drawings on which.

DETAILED DESCRIPTION

The disclosed system is intended to transfer energy from an external source to one or several implanted device. The invention concerns an endosseous implant assembly for percutaneous connection. Most parts of the assembly are assembled in the operating room in order to preserve the living bone surrounding the percutaneous passage.

The proposed percutaneous connection device is preferably intended to transfer energy or matter (such as fluids) is designed to be fixed in an osseous structure of a patient to connect an internal entity (150) located inside the body of the patient to an entity external to said body.

Such percutaneous connection device comprises a percutaneous socket (110) having a first end comprising a percutaneous abutment (111) and a second end opposite to the first end.

It further comprises an elongated extension member (115) intended to be inserted within a hole created into the osseous structure, said extension member (115) having a first end comprising means to be removably coupled to the second end of the socket (110), and a second end opposite to the first end. The extension member is thus designed and adapted for insertion within a bone hole, the corresponding shape and material of such extension member being thus specifically provided for easing the cooperation with the bone structure of the bone hole.

Figure 5A:
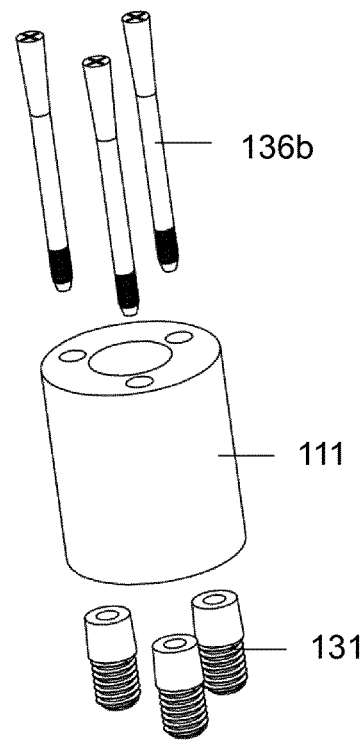
FIG. 5A is an isometric projection of an endosseous percutaneous connector assembly according to a second embodiment of the invention, wherein there are three screw maintaining elements and wherein there are three implants.
Figure 5B:
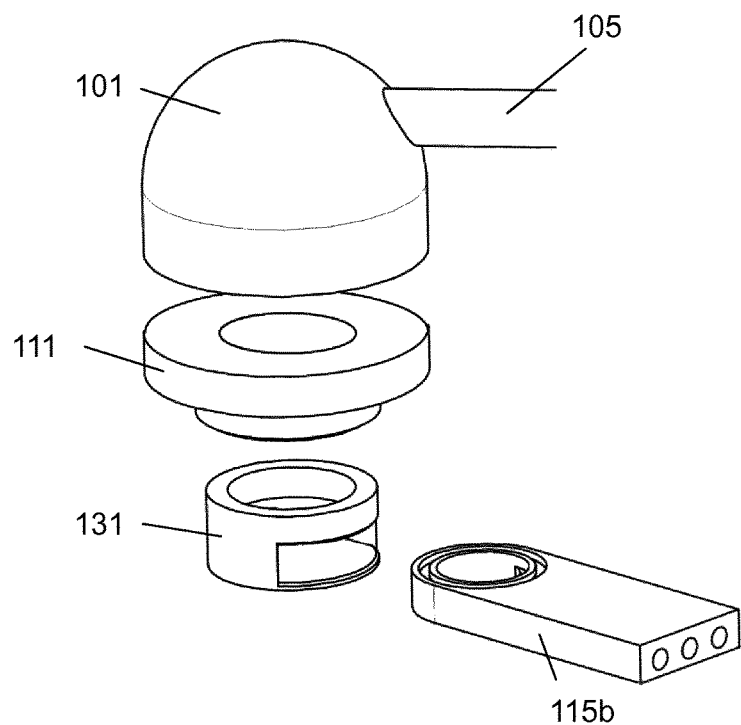
FIG. 5B is an isometric projection of an endosseous percutaneous connector assembly according to a third embodiment of the invention, wherein the extension is a quadrilateral housing
Figure 5C:
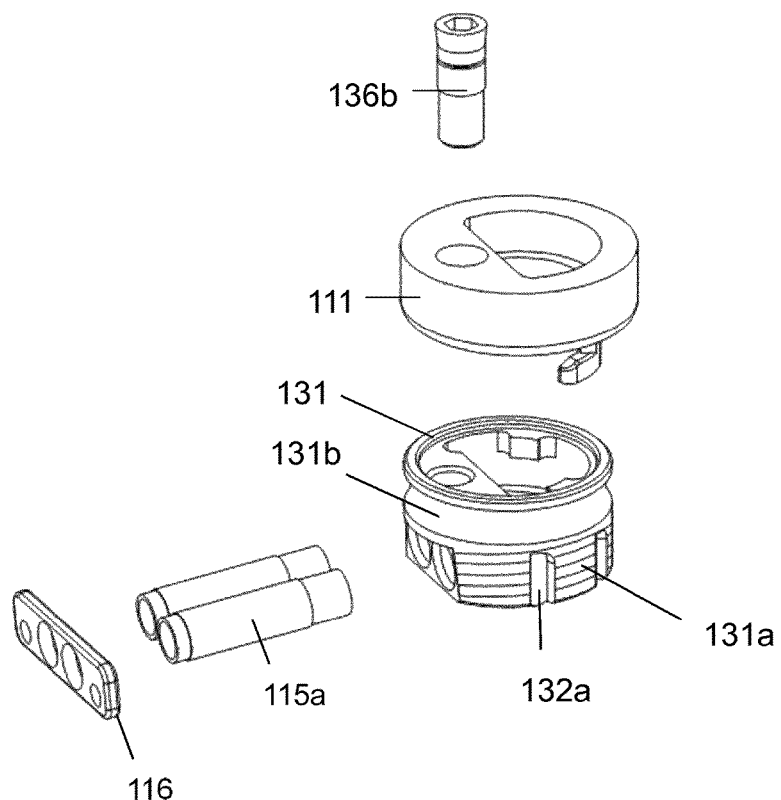
FIG. 5C is an isometric projection of an exploded view of an endosseous percutaneous connector assembly according to a fourth embodiment of the invention, wherein the maintaining element is a screw, the implant is a self-taped threaded system and the extension is made of two separate tubes.

Preferably, the removable coupling of the elongated extension member (115) relative to the percutaneous socket (110) is designed for angular shifting of the first end of the percutaneous socket (110) relative to the second end of the extension member (115). Such angular shifting ($\alpha$) is illustrated in FIG. 5F for instance. Preferably, the angular shifting of the first end of the percutaneous socket (110) relative to the second end of the extension member (115) is at least of 70°. Most preferably the angular shifting is lower than 110°. The angular shifting may for instance be an angle $\alpha$ of a value comprised between 90° and 100°, and preferably an angle $\alpha$ of 95°.

The device also comprises anchoring means provided for anchoring the device to the osseous structure, such anchoring means being preferably designed for enabling the device to be osseointegrated.

Finally, there are provided specific separate connection means running through the device from the first end of the percutaneous socket (110) to the second end of the extension member (115), said connection means comprising at least a first connector (130) arranged within the percutaneous abutment (111).

The specific arrangement which is proposed, in particular the angular shifting provided with the fact that the extension member is elongated, enables moving an end of the connection elements away from the percutaneous passage, which reduces the risks of infections at this passage.

The endosseous positioning of the extension member, coupled with the anchoring of the whole device, in particular at the second end of the percutaneous socket (110) enables having a firmly anchored percutaneous connection device, limiting the risks of movement of the connection elements.

Further, as it will be apparent from the description below, the device is designed for easing a quick implantation in the bone cavity of the patient, consequently reducing the duration of the surgical procedure which is of great advantage.

Contrary to some prior developed devices for percutaneous connection, this device enables a full implantation in a single surgical step, all the while significantly reducing the risks of post-surgery infections.

In particular, the proposed percutaneous connection device does not require a bone augmentation around the percutaneous passage, which is very advantageous as it is mostly operational as soon as it has been implanted in the patient, without requiring a long time for bone healing for instance.

In one embodiment, the extension member (115) is removably fastened to the percutaneous socket (110), and the anchoring means are arranged at the second end of the percutaneous socket (110), said second end of the percutaneous socket (110) being designed for osseous burial in the osseous structure so that the percutaneous abutment (111) protrudes relative to the surface of the osseous structure.

In another embodiment, the percutaneous socket (110) is removably fastened to the extension member (115), and the anchoring means are arranged at the first end of the extension member (115), close to the removable coupling of the extension member (115) relative to the percutaneous socket (110).

In still another embodiment, the extension member (115) and the percutaneous socket (110) are removably coupled via an anchoring base comprising the anchoring means, said anchoring base being designed for osseous burial in the osseous structure and comprising first coupling means for removable fastening of the percutaneous abutment (111) intended to protrude relative to the surface of the osseous structure, and second coupling means for removable fastening of the extension member (115) intended to be fully buried in the osseous structure.

In this latter embodiment, the anchoring base may comprise an implant (131) having a cylindrical or truncated-conical shape. The implant has preferably at least a partial hollow shape, being for instance provided with a blind-hole adapted to receive the percutaneous abutment (111). Such implant is further designed with at least one hole provided in one of the walls of the implant (131), preferably a lateral wall of the implant, in order to receive the extension member.

Most preferably, the percutaneous abutment (111) has thus a shape to be at least partially inserted in the implant (131). The first end of the elongated extension member (115) may also comprise means to be removably inserted within the hole of the implant (131).

In a specific embodiment, the percutaneous connection device comprises:
  an implant (131) having a cylindrical or truncated-conical shape, said implant (131) forming an anchoring base with anchoring means for anchoring of the device in the osseous structure, and said implant having at least one lateral hole provided in a lateral wall of the implant (131);
  a percutaneous abutment (111) having a shape to be at least partially inserted in the implant (131), preferably in a removable manner;
  an elongated extension member (115) intended to be inserted within a hole created into the osseous structure, said extension member (115) having a first end comprising means to be removably inserted within the lateral hole of the implant (131), and a second end opposite to the first end; and connection means running through the device from the percutaneous abutment (111) to the second end of extension member (115), said connection means comprising at least a first connector (130) arranged within the percutaneous abutment (111).

As is illustrated in FIGS. 4A, 4B, 5A, 5C the implant (131) may comprise a threaded portion for implantation into the osseous structure. It may further comprise a ring portion at one end of the implant for tightening and adjusting the position of the implant (131) into the osseous structure.

The ring portion may comprise at least one lateral flat portion. The ring portion has preferably a polygonal external shape, preferably an octagonal or hexagonal external shape. The ring portion can also be of a substantially cylindrical shape.

Figure 5D:
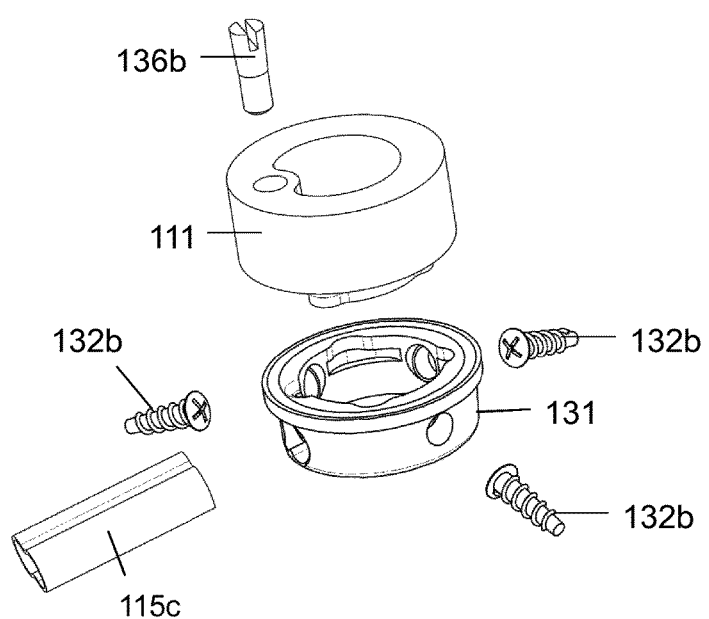
FIG. 5D is an isometric projection of an exploded view of an endosseous percutaneous connector assembly according to a fifth embodiment of the invention, wherein the maintaining element is a screw, the implant is an impacted system associated with lateral screws, and the extension is a single-piece element created from the intersection of the two tubes.
Figure 5E:
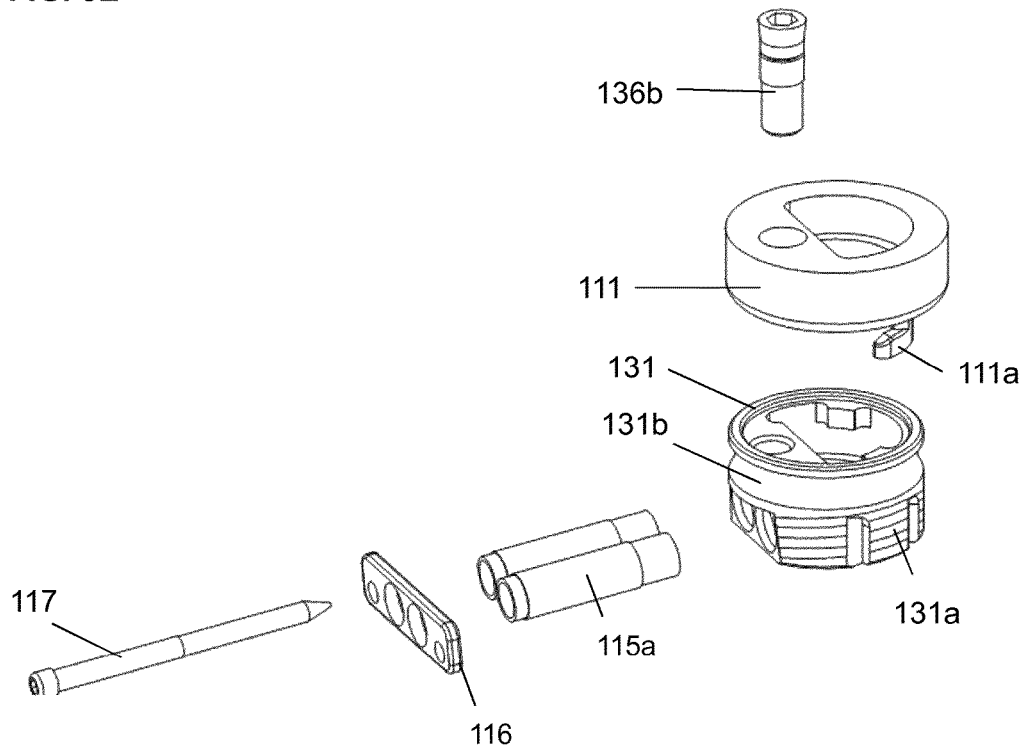
FIG. 5E is an isometric projection of an exploded view of the device of FIG. 5C, with a complementary stabilization shaft.
Figure 5F:
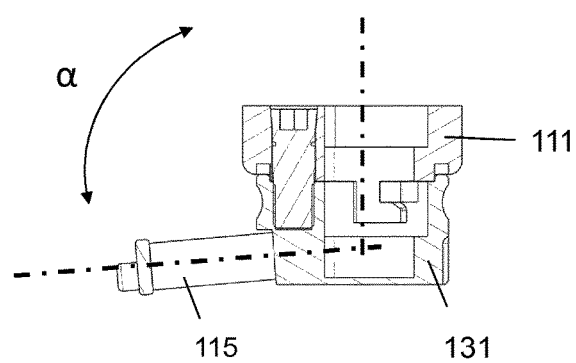
FIG. 5F is a cross-sectional view of the device of FIG. 5D, illustrating the angular shifting.

In another embodiment as illustrated in FIG. 5D, the implant (131) may comprise a plurality of anchoring holes provided in a lateral wall of the implant (131), each of said anchoring holes being intended to receive an osteosynthesis screw (132b) for anchoring the implant into the osseous structure.

Preferably, the abutment (111) of the percutaneous connection device according to any embodiment comprises a through hole for reception of the first connector (130), said through hole having a shape designed for guiding positioning of the first connector (130) within the abutment (111). Such shape is a "mistake-proofing" shape, also called "poka-yoke" shape, which prevents any wrong positioning of the connector (130) within the abutment (111).

Preferably the abutment (111) is partly and/or totally cylindrical, triangular and/or polygonal.

The anchoring means of the device may have several alternative or complementary features.

Figure 6A:
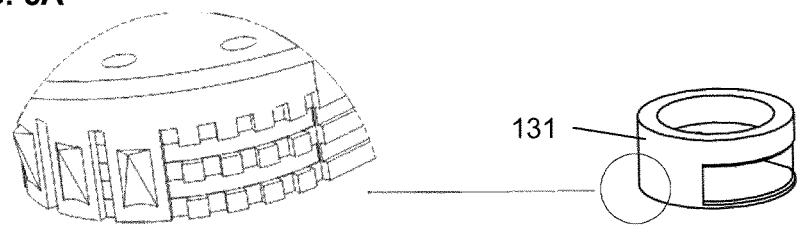
FIG. 6A to FIG. 6C are isometric projections of anchoring means provided on the endosseous implant designed to be impacted in the bone.
Figure 6B:
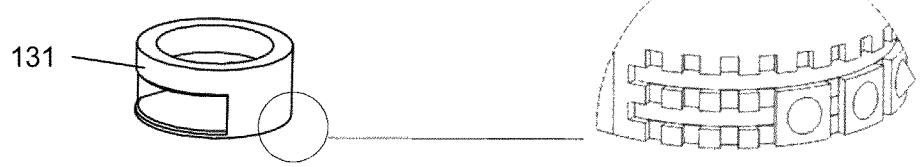
Figure 6C:
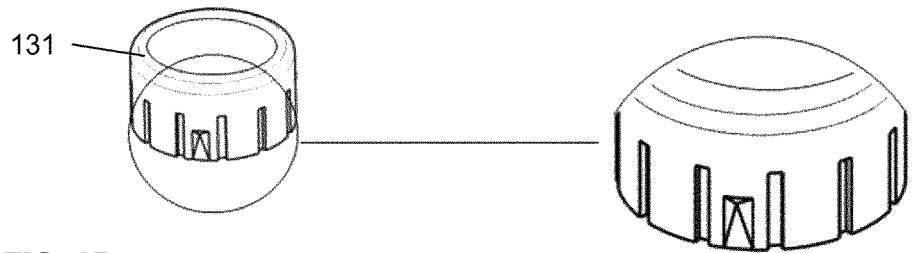
Figure 6D:
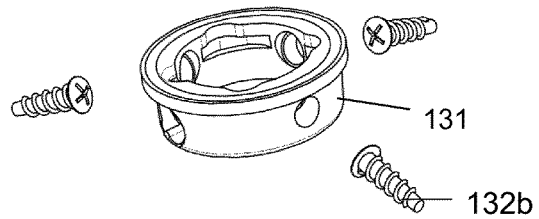
FIG. 6D is an isometric projection of an alternative anchoring means for the endosseous implant, wherein the implant is designed to be impacted in the bone and fixed by stabilization screws.

The anchoring means may for instance comprise a plurality of osteosynthesis screws (132b) as illustrated in FIG. 5D or FIG. 6D. The implant is designed so that the osteosynthesis screws protrude relative to the surface the device in order to mesh with a lateral wall of a cavity of the osseous structure.

The anchoring means may also comprise any other anchoring element arranged so as to be able to protrude relative to the surface the device in order to mesh with a lateral wall of a cavity of the osseous structure. For instance, the anchoring means may comprise a threaded surface as illustrated in FIG. 4B, FIG. 5C, FIG. 5E, or FIG. 6E. Such threaded surface is adapted for easing primary anchoring of the device in the osseous structure.

The anchoring element may also comprise projecting portions as illustrated in FIG. 6A to 6C, said projecting portions being designed to penetrate the lateral wall of the cavity in a depth between 20 micrometers and 2000 micrometers, and preferably in a depth of 400 micrometers.

Preferably, the projecting portions have a geometric shape to provide a retention effect, said shape being preferably a symmetric shape chosen among a cone shape, a pyramid shape, and/or a polyhedron shape.

Preferably, the percutaneous socket (110), the percutaneous abutment (111), the implant (131), and/or the extension member (115) are made of titanium, polyether ether ketone, zirconia and/or any biocompatible material.

For instance, the implant can be made of titanium using machining and/or additive manufacturing processes.

The implant (131) and/or the extension member (115) may also be coated with a coating for promoting osseointegration of the device into the osseous structure.

There are several solutions for connecting the percutaneous abutment (111) to elements external to the patient. For instance, the percutaneous abutment (111) can be connected mechanically, magnetically, and/or physically to one or multiple external parts.

Preferably the first connector (130) is clipped within the percutaneous abutment (111) with a non-return system.

Additionally or alternatively, the first connector (130) is maintained in position within the percutaneous abutment (111) with a maintaining element (136) inserted within the percutaneous abutment (111).

Figure 4A:
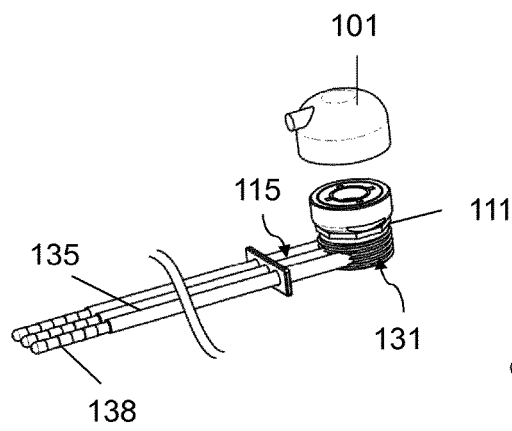
FIG. 4A is an isometric projection of the percutaneous connector assembly according to another embodiment of the invention.
Figure 4B:
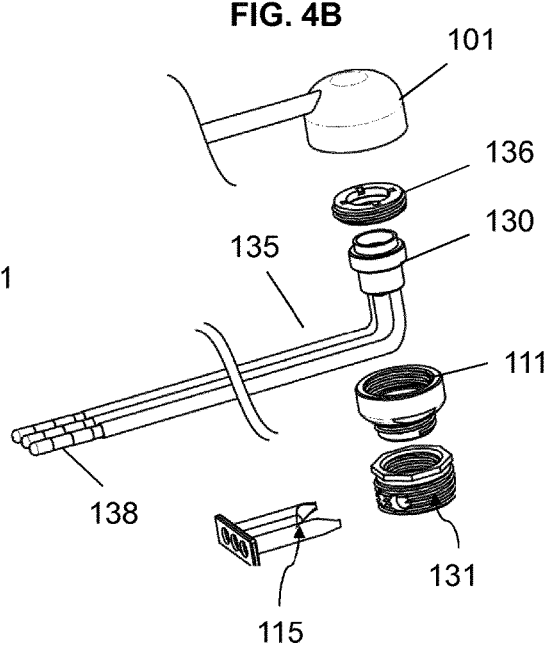
FIG. 4B is an isometric projection of an exploded view of the percutaneous connector assembly of FIG. 4A.

Such maintaining element may for instance be a ring (136) as illustrated in FIG. 4B, screwed or pushed in the abutment (111), said ring preferably comprising a cutting on the inside in order to place an O-ring to maintain the first connector (130) in compression.

For all embodiments of the percutaneous connection device, the shape of the elongated extension member (115) may differ. For instance, the extension member (115) can have a tubular lumen geometry, said tubular lumen geometry being chosen among parallelepipedal, regular polygonal, irregular polygonal, ovaloid, round or a combination thereof.

Preferably, the extension member (115) comprises a plurality of tubes, such tubes being for instance arranged parallel to each other.

The first connector (130) can be connected to an intermediate connector by a ribbon cable made of biocompatible electrical wires, encapsulated with silicon or any other material that is both flexible and biocompatible.

Further, the percutaneous connection device may comprise an intermediate connector intended to be connected to the internal entity, wherein said intermediate connector comprises a screw or pin system to lock and seal the intermediate connector. Additionally or alternatively, the intermediate connector comprises at least one eyelet on each side, said eyelets being used to attach the implant to the bone with screw and/or suture the implant to the fascia. Preferably, the intermediate connector is a subcutaneous connector.

The connection means also comprises a second connector (138) arranged at the opposite end of the connection means relative to the first connector (130), said second connector (138) having a shape designed to pass through the percutaneous socket (110) and the extension member (115).

Preferably, the connection means are electrical connection means, and the first connector (130) and/or the second connector (138) are jack connectors, preferably having a cross-section being circular or in cross arrangement.

Figure 1A:
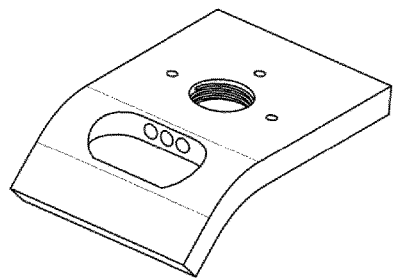
FIG. 1A to 1J schematically illustrate one example of the positioning of the different elements of a percutaneous connection device in a calvaria, i.e. in the dome of the skull of a patient.

As is apparent from above and from the figures, the percutaneous connection assembly may include some of the following elements:

An external connector (101);
An external cable (105);
An abutment (111);
A connection element (130);
One or several maintaining element (136);
An endosseous implant (131);
An extension (115);
A stabilization shaft (117);
One or several implanted cables (135);
An intermediate connector (138 and 140);

During the surgical procedure for implanting the percutaneous connection device, the surgeon drills with a template a first hole in the bone that will receive the endosseous implant (131). Then, a template is used to drill a second hole, and one or several tunnels are drilled between the two said holes (FIG. 1A). Then, the different elements of the device are positioned in the bone structure (FIG. 1B to FIG. 1F.)

FIG. 1A to 1J schematically illustrate one example of the positioning of the different elements of a percutaneous connection device in a calvaria, i.e. in the dome of the skull of a patient.

Figure 1B:
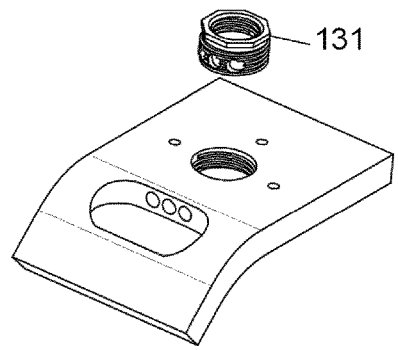
Figure 1C:
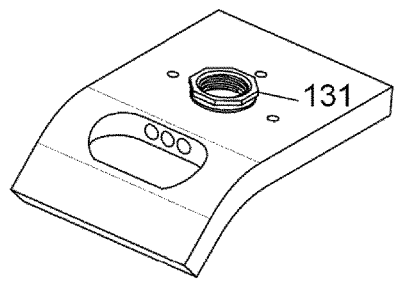

- In a first step illustrated on FIG. 1A, several holes are drilled in the calvaria of the patient, with one or several templates.
- In a second step illustrated on FIG. 1B, the implant (131) of the percutaneous connection device is implanted in the surgically prepared bone cavity of FIG. 1A. On FIG. 1C, is illustrated the implant (131) inserted in the surgically prepared bone cavity of FIG. 1A.
- In a third step illustrated on FIG. 1D the elongated extension member (115) of the percutaneous connection device according to one embodiment of the invention is inserted in bone channel holes. On FIG. 1E, is illustrated the elongated extension member (115) inserted in bone channel holes.
- In a fourth step illustrated on FIG. 1F, the abutment (111), the electrical connection element (130) and the corresponding electric cables (135) of the percutaneous connection device are inserted through the implant (131) and the extension (115). On FIG. 1G is illustrated the abutment of FIG. 1F fixed to the implant (131), and on FIG. 1H is illustrated the electrical connection element (130) completely inserted in the abutment (111).
- Finally, in a fifth step illustrated on FIG. 1I the maintaining element (136) is inserted on the electrical connection element (130). On FIG. 1J is illustrated the maintaining element (136) inserted and fixed on the electrical connection element (130).

On FIG. 2A to 2H are illustrated in more details—on cross-sectional views—the first step of preparing the bone structure, and the further steps of positioning the elements forming the percutaneous connection device.

Figure 2A:
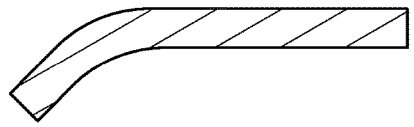
FIG. 2A to 2H are cross-sectional views of the calvaria, illustrating in more details the first step of preparing the bone structure, and the further steps of positioning the elements forming the percutaneous connection device.

On these figures, FIG. 2A represents a simplified partial calvaria before any drilling of holes.

Figure 2B:
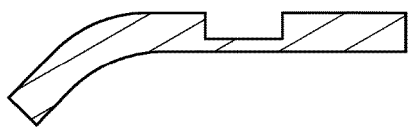

FIG. 2B illustrates the first step of the drilling, wherein the bone hole receiving the implant of the percutaneous connection device has been drilled.

Figure 2C:
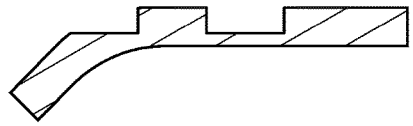

FIG. 2C illustrates a second step of the drilling, wherein the bone hole letting the exit driveline pass has been drilled, in addition to the bone hole receiving the implant.

Figure 2D:
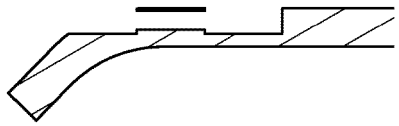

FIG. 2D illustrates a third step of the drilling, wherein the bone holes channel under the outer table for the elongated extension member have been drilled, in addition to the bone hole receiving the implant and the bone hole letting the exit driveline pass.

Figure 2E:
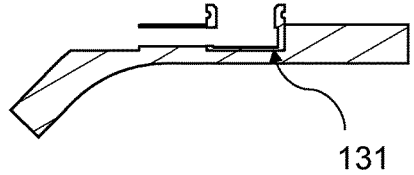

FIG. 2E is a view of the skull with the implant (131) of the percutaneous connection device having been inserted in the bone cavity.

Figure 2F:
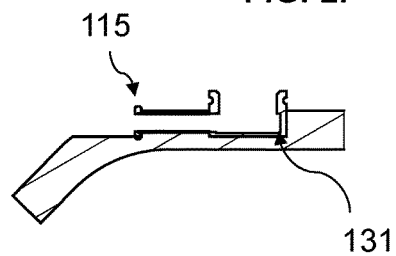

FIG. 2F is a view of the skull with the extension member (115) of the percutaneous connection device inserted in the corresponding bone holes, and coupled with the implant (131).

Figure 2G:
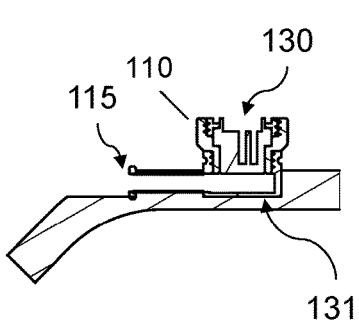

FIG. 2G is a view of the skull with the abutment (111) comprising the electrical connection element (130) coupled to the implant (131).

Figure 2H:
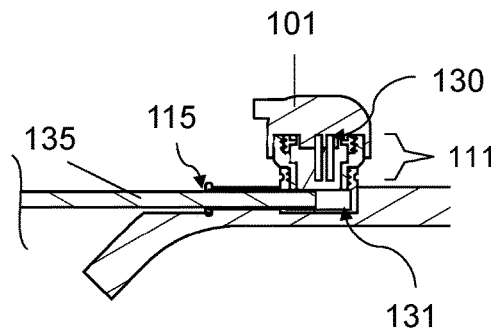
Figure 3A:
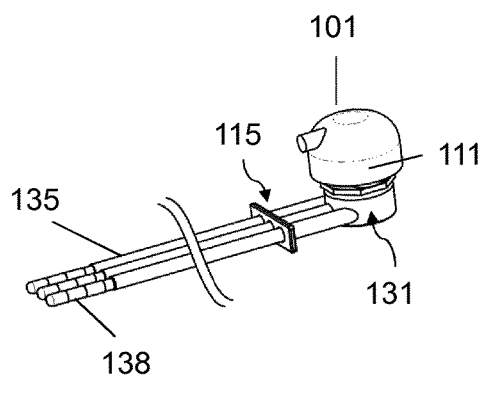
FIG. 3A is an isometric projection of the percutaneous connector assembly according to the first embodiment of the invention, showing all the elements composing the assembly.
Figure 3B:
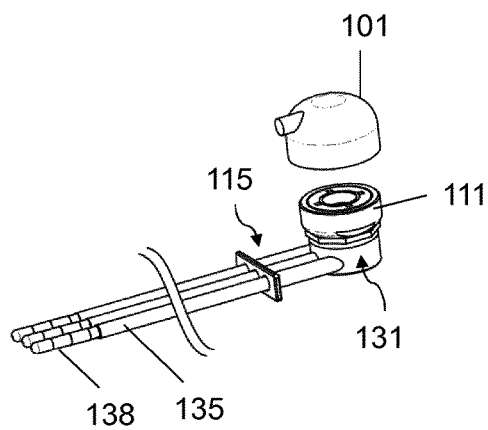
FIG. 3B is an isometric projection of the percutaneous connector assembly of FIG. 3A, showing the external connector unplugged.

FIG. 2H is a view of the skull with the connector (130) and the corresponding connection wires (135) running through the implant (131) and extension member (115), and with the external connector (101) positioned on the abutment (111).

The following description is made more specifically in reference to the appended figures.

The implant (131) preferably comprises a main portion (131a), which is preferably a cylindrical or truncated conical shaped element, and that can be pieced by one or several holes on its lateral side. Such main element of the implant can also be surmounted by a substantially cylindrical ring, or a polygonal ring preferably a hexagonal ring. This ring permits to tighten and to adjust the implant in the bone with a torque wrench.

The main element (131a) is preferably tapped in order to place a threaded ring to maintain the connection.

Figure 6E:
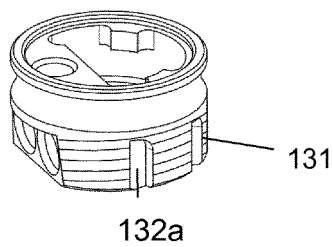
FIG. 6E is an isometric projection of an alternative embodiment of the endosseous implant its surface is threaded with a self-tapping system.

The main element (131a) comprises anchoring means. In a first embodiment, the main element (131a) is threaded on its outside surface in order to screw the implant in the bone. To reduce the duration of implantation a self-tapping system (132a) can be considered (FIG. 5C and FIG. 6E).

To optimize the osseointegration and minimize the risks of bone depression the height and width range of the thread could be shorter at the top of the main element than at the middle and the bottom of the main element (not shown in the figures).

In a first alternative embodiment, the anchoring means consist of projected and/or indent elements at the surface of the main element (FIG. 6A to 6C). These anchoring means can maintain the implant in an osseous structure after an impaction of said implant (131) thanks to a harpoon effect or similar physical phenomenon.

In a second alternative embodiment, a cam system such as described in patent application FR 11-50639 and one or several screws connected to the main element (131a) can be used as anchoring means.

In a third alternative embodiment (FIG. 6D) the implant is designed to be impacted in the bone and fixed by stabilization screws (132b) to guarantee the primary stability. Having a strong primary stability promotes the osseointegration of the whole device which is advantageous. Moreover, the implant may have a soft conical shape or tapered shape which promotes impaction of the implant in the bone structure when the screws are tightened up.

In a fourth alternative embodiment, one or several threaded implants (131) are screwed in the bone. These implants may be maintained together by a plate (not shown in the figures).

In the embodiment illustrated in FIG. 5A, there are several threaded implants (131) that are to be screwed in the bone, and form all together the anchoring base of the device. In this particular embodiment there are three implants but there can be more implants used. An abutment is then fixed by one or several screws (136b) on the implants (FIG. 5A). An extension (not shown in the figures) can be place between two implants. Alternatively, a narrow bone trench could be used to place directly the electrical wires.

The main element (131a) aims to generate a mechanical torque when the implant is tightened.

The implant (131) can be made of titanium or other biocompatible materials which can favor osseointegration.

The implant (131) may have a coating on the surface to ensure osseointegration.

The implant (131) may have a groove above the main element in order to obtain a larger contact surface for the skin.

The implant (131) may have a retaining element to get a depth stop. This retaining element is above the main element and under the said groove. A flange can top the implant (131) and protrude to the surface of the bone.

Figure 1D:
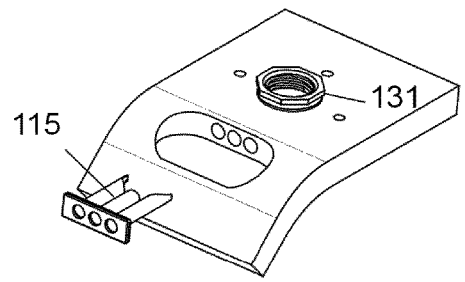
Figure 1E:
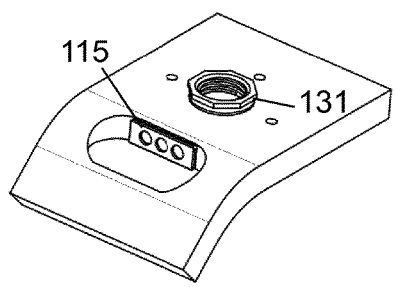

An extension member (115) is fixed to the implant through the holes located on the lateral side of the implant (FIG. 1D). Alternatively the holes can be located at the bottom-end of the implant. The extension member (115) may be made of titanium or other biocompatible materials which can favor osseointegration.

Said extension member (115) prevents a direct contact between the bone and the overmolded cable. It also prevents a bone growth in the bore.

The extension member (115) may have a coating on the surface to ensure osseointegration.

The extension is preferably solid to preserve the cranium mechanical properties and protect the cable in case of trauma.

In a first embodiment, the extension member (115) is made of several tubes. These tubes may have a joint extremity (116) to facilitate their insertion. For instance, the tubes (115) may be flexible.

The tubes may have mechanical means to be clipped-in in the implant.

In a second embodiment, the extension member (115) is made of quadrilateral housing (115b) as illustrated on FIG. 5B. This housing may include an opening on its top side and one or several opening on its lateral extremity. The extremity side being inserted in the implant is preferably concave. The housing (115b) may have corners that are rounded shaped (not shown in the figures). Alternatively this housing shape can be a tube. The housing (115b) may have anchoring means to maximize its stability preferably on its lateral sides. The surface of the housing (115b) may include coatings or any other structure to favor bone growth into its surface.

In a third embodiment, the extension member (115) is a flexible structure. Technical solutions considered include sheathing or titanium mesh.

An abutment (111) is mechanically fixed. In a first embodiment, it can be secured by different means: screwed (FIG. 1F to 1H) or pushed in the implant (131).

Said abutment (111) is preferably composed by two parts: a threaded cylinder surmounted by a tapped cylinder with a bigger diameter.

According to one embodiment, the upper cylinder contains two flat spots on the outside. This two flat spots are used for tightening the abutment on the implant and for mechanical coding (poka yoke) for the external connector. The abutment (111) may have more than two flat spots in order to improve the tightening of the mechanical torque transmission.

The abutment (111) may also present one or several different geometrical recess in order to insert an instrument with the negative shape. The abutment (111) may also present one or several identical geometrical recess in order to insert an instrument with the negative shape.

The abutment (111) may have a coating to favor epithelial seal. The abutment (111) may have a mistake-proofing geometry in the intern part. This element prevents the rotation of the connection element (130) inside the abutment (111). The abutment (111) also may have an anti-loosening system based on a deformable part or on a blocking part.

A stabilization shaft (117) may be used to maintain the tubular extension fixed to the implant and prevent any implant rotation. The shaft is preferably threaded at the extremity in order to be screwed in the implant.

Figure 1F:
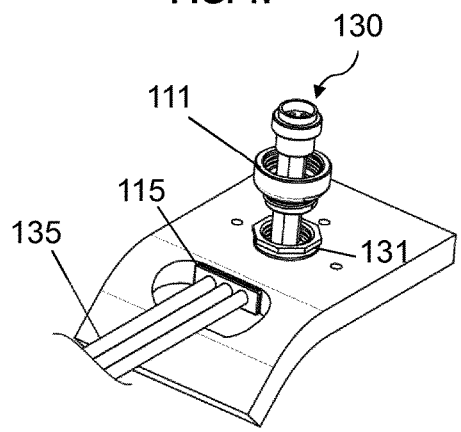
Figure 1G:
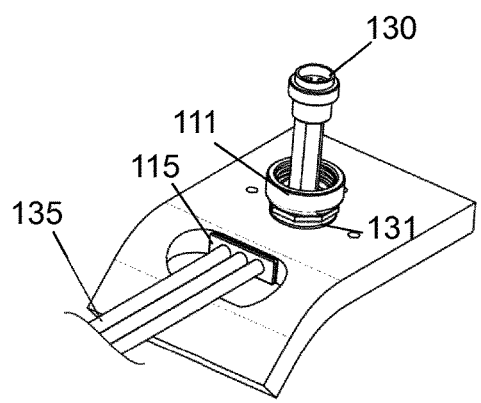
Figure 1H:
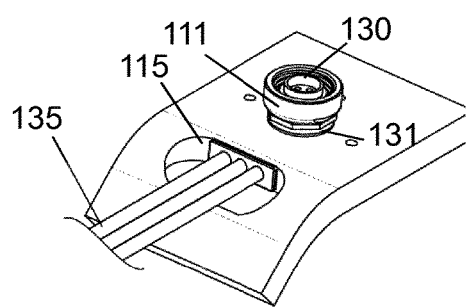

A connection element (130) is preferably inserted in said abutment (111). Two support rings, monobloc with the abutment (111), are maintaining the connection element (130) inside the abutment (111). The connection element (130) is composed of a cylindrical or polygonal connector from which come out one or several cables. Those cables pass through the tubular extension osseointegrated in the bone (FIG. 1F to 1H).

At the end of each cable is provided the first end of the intermediate connector (138).

In a first embodiment, these connectors may be in-line connectors, flexible and designed to facilitate their passage through the apertures of the implant (131). These in-line contacts connectors can embed various ranges of contacts. The number of in-line contacts connectors and the number of contacts considered varies depending on the internal entity.

Two combinations are particularly considered: the first combination is three cables with two contacts each; the second combination is two cables with 3 contacts and one cable with two contacts.

Each in-line contacts connectors preferably comprise a geometrical mistake-proofing (poka yoke) in order to avoid a connection in the wrong connector.

Any other combinations can be considered depending on the number of contacts required by the internal entity (150).

In a first embodiment, the in-line contacts might be annular as shown in the FIGS. 3A, 3B, 4A, 4B, 8A and 8B. In order to minimize heat dissipation due to energy transfer, in a second embodiment, the in-line contacts might not be annular hence maximizing the contact area (not shown in the figures). Cross-headed pins or other pins made of one or several blades are geometries that can be considered.

Figure 7:
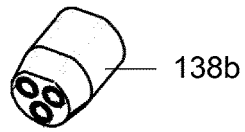
FIG. 7 is an isometric view of the first end of the intermediate connector in its circular connector embodiment.
Figure 8A:
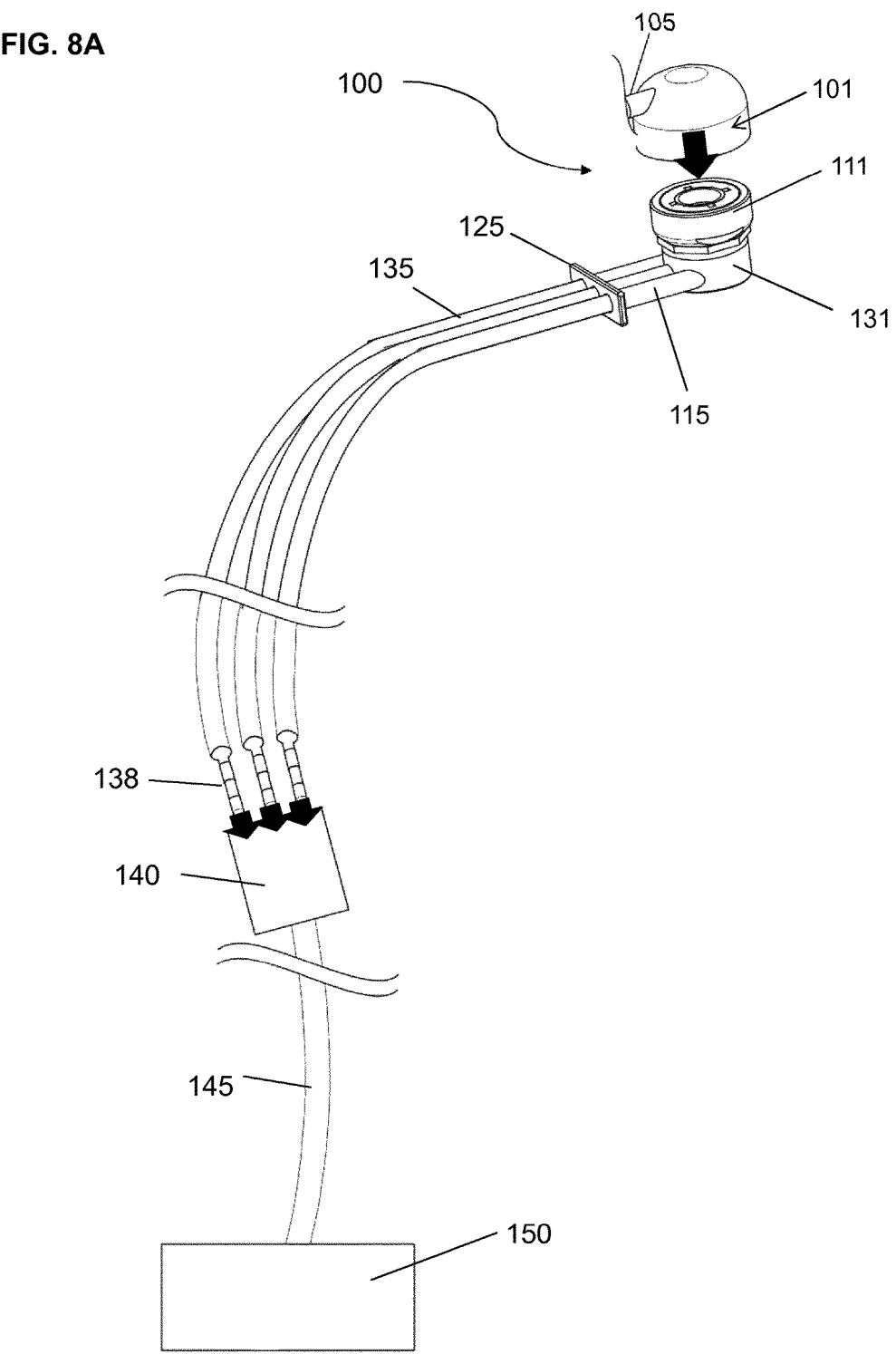
FIG. 8A and FIG. 8B are global views of the permanent percutaneous connection device of the invention comprising a cranial connection assembly and an intermediate thoracic connection assembly.
Figure 8B:
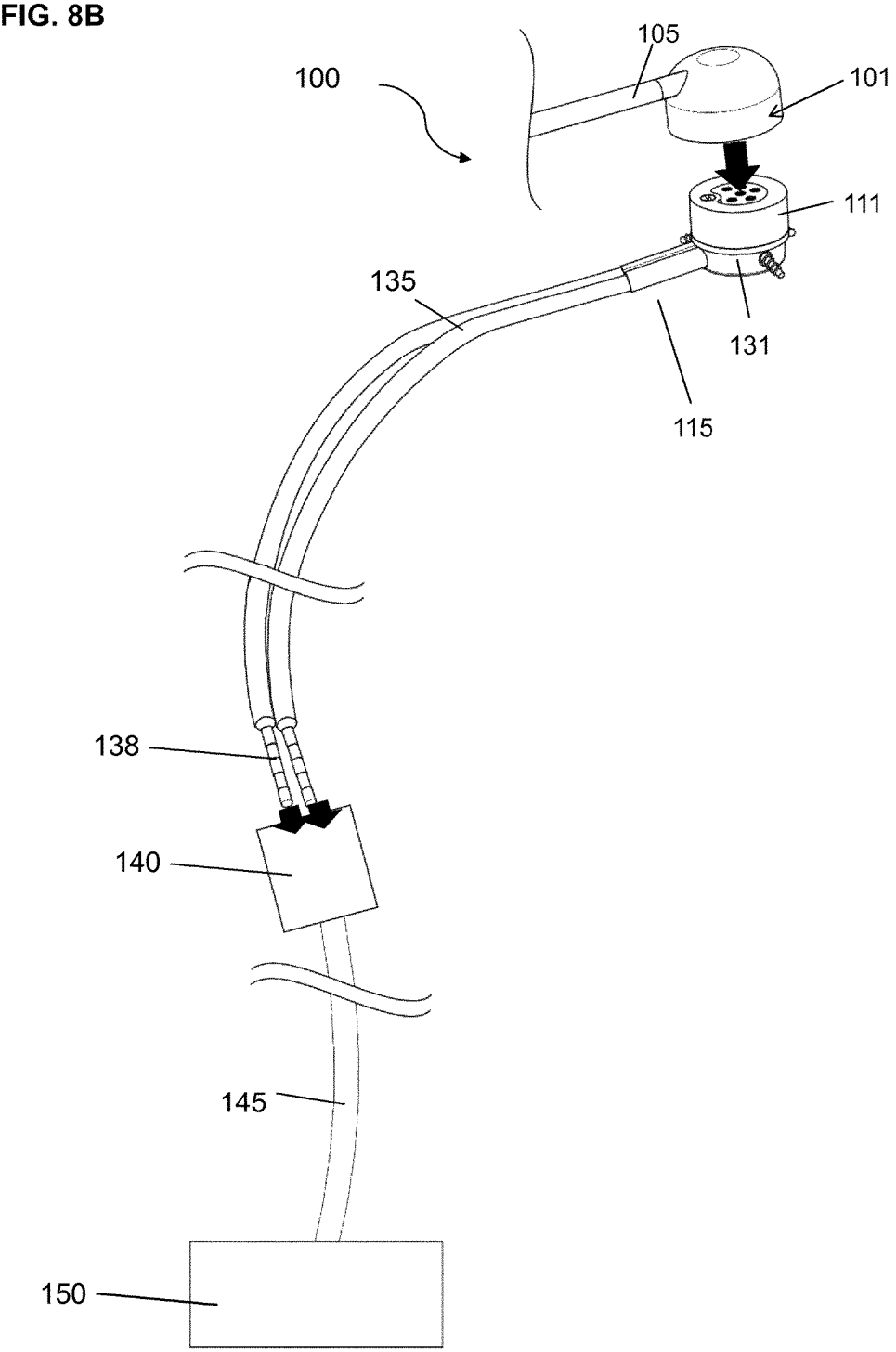

In a second embodiment (FIG. 7), the first end of the intermediate connector may be circular connectors (138b).

The connection element (130) is maintained in the abutment (111) by one or several maintaining element.

Figure 1I:
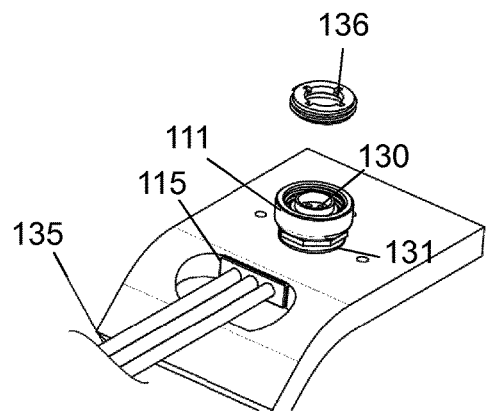
Figure 1J:
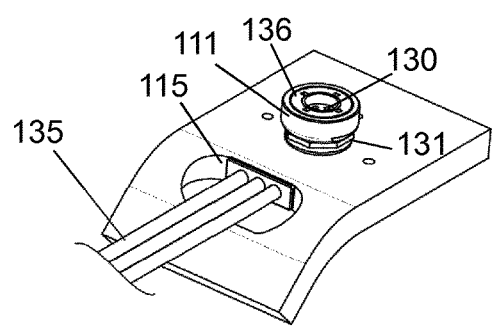

In a first embodiment, the maintaining element could be a ring maintaining element (136a) screwed or pushed in the abutment (111), or the connector could be clipped with a non-return system (111a) provided on the abutment. The ring (136a) may contain a cutting on the inside in order to place an O-ring to maintain the connector in compression (FIG. 1I-1J).

In a second embodiment, the maintaining element could be one or several screw maintaining elements (136b) screwed or pushed in the abutment (111) (FIGS. 5A, 5C and 5D).

One or several implanted cables (135, 145) connect the connection element (130) to the internal entity (150) or internal entities (146 and 150).

In a first embodiment shown in the figures, implanted cables (135) start with the connection (130) and end with the first end of the intermediate connector (138). The connection (130), the implanted cables (135) and the in-line contacts are monobloc. The connection (130) is connected to the external connector (101) and hosted in the abutment (111) and the implant (131). The first end of the intermediate connector (138) is connected with the second end of the intermediate connector (140) which extends from the internal entity (150).

In a second embodiment not shown in the figures, the connection (130) is made of in-line contacts. The implanted cables (135) connect directly the connection (130) to the internal entity (150), there is no intermediate connector (138 and 140).

The second end of the intermediate connector (140) is protected by a housing made of titanium or other biocompatible materials comprising multiple contacts and electrical wires and/or optical fibers.

The connector (140) is preferably implanted under the skin in thoracic subclavian region. Alternatively it can be implanted anywhere close to the first internal entity. For example it can be placed in the pericardial area if the internal entity is placed there.

An external connector (101) is magnetically and/or mechanically (including clipped, screwed or pushed in) fixed to the abutment (111) and rely the percutaneous system (100) to the external batteries or controller via an external cable.

The external connector (101) is a cylindrical or a polygonal part comprising multiple contacts and electrical wires.

Several configurations are possible to power the internal entity (150) through a percutaneous connector (100).

Figure 9A:
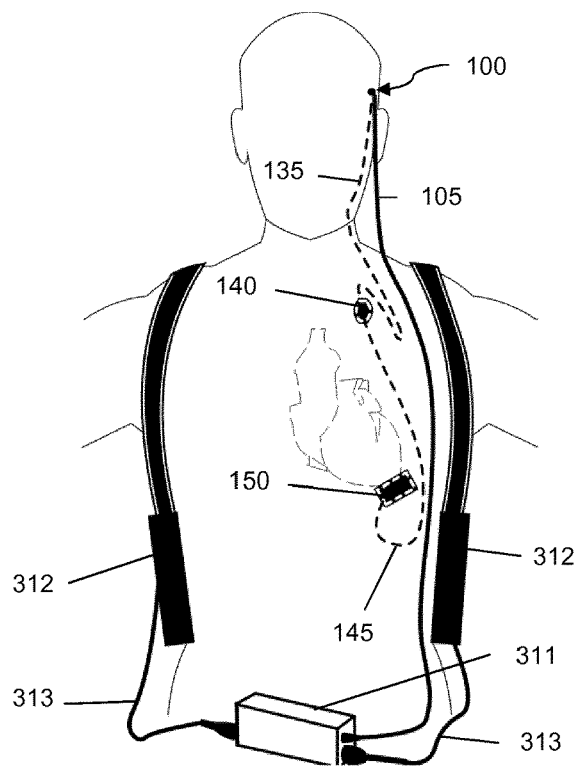
FIG. 9A illustrates a schematic front view of a patient being implanted with an internal entity and equipped with a percutaneous connector and external components.

In a first embodiment illustrated in FIG. 9A, the internal entity (150) is directly connected to the external controller (311) and the external batteries (312) through the percutaneous connector (100) with external cables (313). An implanted electric connection element (130), and an intermediate connector (138 and 140) may facilitate the change of the cervical electric cable (135) or the implanted entity (150).

Figure 9B:
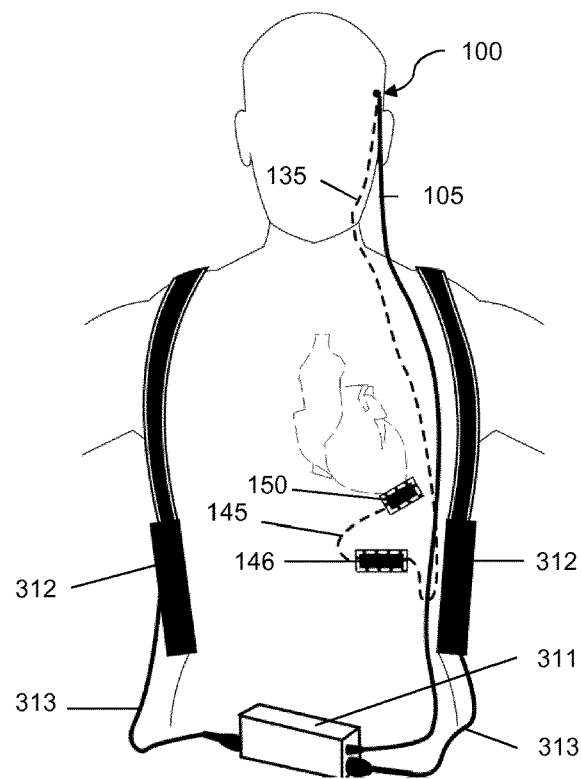
FIG. 9B illustrates a schematic front view of a patient being implanted with a fully implanted system comprising two internal entities, one of which hosting a controller and a battery and being connected to a percutaneous connector, and wherein the implanted battery and implanted controller can be hosted in the same housing.

In a second embodiment illustrated in FIG. 9B, the percutaneous connector (100) can be used with a fully implanted system wherein the implanted battery and the implanted controller are both hosted in a second internal entity (146). In this configuration the patient can remove the external components (105, 311, 312), and rely only on the implanted battery and controller for a limited period of time. External batteries (312) can be used as a backup supply in order to charge the implanted battery via the percutaneous connector (100). An external controller (311) can be used as a back-up controller or used to add additional functions to the system (FIG. 9B).

Figure 9C:
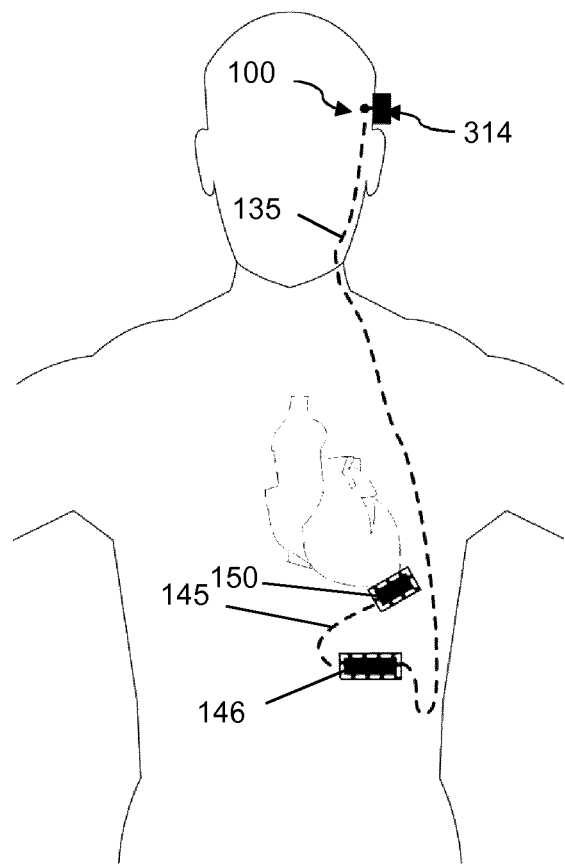
FIG. 9C illustrates a schematic front view of a patient being implanted with two internal entities, one of which hosting a controller and/or a battery connected to a percutaneous connector with a lid.

In another embodiment illustrated in FIG. 9C, the first internal entity (150) is powered by an implanted battery hosted in the second internal entity (146) and the percutaneous connector (100) can host the controller and or the battery. The cranial housing (314) can be a lid on the percutaneous connector or alternatively it can be hosted in a headband or in a helmet (not shown in the pictures).

REFERENCES

U.S. Pat. No. 5,904,646
FR 03-04063
U.S. Ser. No. 12/631,161
FR 11-50639

The invention claimed is:

1. A percutaneous connection device, preferably intended to transfer energy or matter, intended to be fixed in an osseous structure of a patient to connect an internal entity located inside the patient's body to an entity external to said body, wherein the device comprises:
an implanted percutaneous socket having a first end comprising a percutaneous abutment and a second end opposite to the first end;
an elongated extension member designed to be inserted within a hole created into the osseous structure, said extension member having a first end arranged to be removably coupled to the second end of the socket, and a second end opposite to the first end;
anchoring means provided for anchoring the device to the osseous structure by osseointegration; and
separate connection means running through the device from the first end of the percutaneous socket to the second end of the extension member, said connection means comprising at least a first connector arranged within the percutaneous abutment,
wherein the extension member is removably fastened to the percutaneous socket, and the anchoring means are arranged at the second end of the percutaneous socket, said second end of the percutaneous socket being designed for osseous burial in the osseous structure so that the percutaneous abutment protrudes relative to a surface of the osseous structure.

2. The device of claim 1, wherein the anchoring means are arranged at the first end of the extension member.

3. The device of claim 1, wherein the extension member and the percutaneous socket are removably coupled via an anchoring base comprising the anchoring means, said anchoring base being designed for osseous burial in the osseous structure.

4. The device of claim 3, wherein:
the anchoring base comprises an implant having a cylindrical or truncated-conical shape, said implant having at least one hole provided in a wall of the implant;
the percutaneous abutment has a shape to be at least partially inserted in the implant;
the first end of the elongated extension member is shaped to be inserted within the hole of the implant.

5. The device of claim 4, wherein the implant comprises a threaded portion for implantation into the osseous structure, and a ring portion at one end of the implant for tightening and adjusting a position of the implant into the osseous structure.

6. The device of claim 5, wherein the ring portion comprises at least one lateral flat portion.

7. The device of claim 4, wherein the implant comprises a plurality of anchoring holes provided in a lateral wall of the implant, each of said anchoring holes being intended to receive an osteosynthesis screw for anchoring the implant into the osseous structure.

8. The device of claim 4, wherein the abutment comprises a through hole for reception of the first connector, said through hole having a shape designed for guiding positioning of the first connector within the abutment.

9. The device of claim 4, wherein the implant is made of titanium using machining and/or additive manufacturing processes.

10. The device of claim 1, wherein the anchoring means comprises a plurality of osteosynthesis screws intended to protrude relative to a surface the device in order to mesh with a lateral wall of a cavity of the osseous structure.

11. The device of claim 1, wherein the anchoring means comprises at least one anchoring element arranged so as to be able to protrude relative to a surface of the device in order to mesh with a lateral wall of a cavity of the osseous structure.

12. The device of claim 11, wherein the anchoring means comprises a threaded surface, said threaded surface easing primary anchoring of the device in the osseous structure.

13. The device of claim 1, wherein the anchoring means comprises projecting portions, said projecting portions being designed to penetrate the lateral wall of the cavity in a depth between 20 micrometers and 2000 micrometers.

14. The device of claim 13, wherein the projecting portions have a geometric shape to provide a retention effect, said shape being a symmetric shape chosen from a cone shape, a pyramid shape, and a polyhedron shape.

15. The device of claim 1, wherein the percutaneous socket, the percutaneous abutment, and/or the extension member are made of titanium, polyether ether ketone, zirconia and/or any biocompatible material.

16. The device of claim 1, wherein the extension member is coated with a coating for promoting osseointegration of the device into the osseous structure.

17. The device of claim 1, wherein the percutaneous abutment can be connected mechanically, magnetically, and/or physically to one or multiple external parts.

18. The device of claim 1, wherein the first connector is clipped within the percutaneous abutment with a non-return system.

19. The device of claim 1, wherein the first connector is maintained in position within the percutaneous abutment with a maintaining element inserted within the percutaneous abutment.

20. The device of claim 19, wherein the maintaining element is a ring screwed or pushed in the abutment.

21. The device of claim 19, wherein the maintaining element is a ring comprising a cutting in order to place an O-ring to maintain the first connector in compression.

22. The device of claim 1, wherein the extension member has a tubular lumen geometry, said tubular lumen geometry being chosen among parallelepipedal, regular polygonal, irregular polygonal circular, ovaloid, round or a combination thereof.

23. The device claim 1, wherein the extension member comprises a plurality of tubes.

24. The device of claim 23, wherein the tubes are arranged parallel to each other.

25. The device of claim 1, wherein the first connector is connected to an intermediate connector by a ribbon cable made of biocompatible electrical wires, encapsulated with silicon or any other material that is both flexible and biocompatible.

26. The device of claim 1, comprising an intermediate connector intended to be connected to the internal entity, wherein said intermediate connector comprises a screw or pin system to lock and seal the intermediate connector.

27. The device of claim 1, comprising an intermediate connector intended to be connected to the internal entity.

28. The device of claim 1, wherein the abutment is partly and/or totally cylindrical, triangular and/or polygonal.

29. The device of claim 1, wherein the connection means comprises a second connector arranged at an opposite end of the connection means relative to the first connector, said second connector having a shape designed to pass through the percutaneous socket and the extension member.

30. The device of claim 29, wherein the connection means are electrical connection means, and the first connector and/or the second connector are jack connectors.

31. The device of claim 1, wherein the elongated extension member extends along a longitudinal axis of the elongated extension member and the percutaneous socket extends along a longitudinal axis of the percutaneous socket and wherein the longitudinal axis of the elongated extension member and the longitudinal axis of the percutaneous socket define between them an angle α comprised between 70° and 110°.

* * * * *

UNITED STATES PATENT AND TRADEMARK OFFICE
CERTIFICATE OF CORRECTION

PATENT NO. : 10,220,197 B2  
APPLICATION NO. : 14/410872  
DATED : March 5, 2019  
INVENTOR(S) : Pierre Sabin and Pierre-Yves Quelenn Page 1 of 1

It is certified that error appears in the above-identified patent and that said Letters Patent is hereby corrected as shown below:

On the Title Page

Item (73) Assignee:, "PLUGMED HEART (FR)" should read -- UBIPLUG, Saint-Contest (FR) --.

Signed and Sealed this  
Seventh Day of December, 2021

Drew Hirshfeld  
*Performing the Functions and Duties of the*  
*Under Secretary of Commerce for Intellectual Property and*  
*Director of the United States Patent and Trademark Office*